United States Patent
Peterson et al.

(10) Patent No.: US 10,191,726 B2
(45) Date of Patent: Jan. 29, 2019

(54) BIOSEQUENCE-BASED APPROACH TO ANALYZING BINARIES

(71) Applicant: Battelle Memorial Institute, Richland, WA (US)

(72) Inventors: Elena S. Peterson, Richland, WA (US); Christopher S. Oehmen, Richland, WA (US); Aaron R. Phillips, Richland, WA (US); Darren S. Curtis, West Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 241 days.

(21) Appl. No.: 15/130,837

(22) Filed: Apr. 15, 2016

(65) Prior Publication Data

US 2017/0344352 A1    Nov. 30, 2017

Related U.S. Application Data

(60) Provisional application No. 62/149,126, filed on Apr. 17, 2015.

(51) Int. Cl.
| | | |
|---|---|---|
| *G06F 9/44* | (2018.01) | |
| *G06F 8/53* | (2018.01) | |
| *G06F 8/75* | (2018.01) | |
| *G06F 8/41* | (2018.01) | |
| *G06F 21/56* | (2013.01) | |
| *G06F 21/64* | (2013.01) | |
| *G06F 19/22* | (2011.01) | |

(52) U.S. Cl.
CPC ............... *G06F 8/53* (2013.01); *G06F 8/427* (2013.01); *G06F 8/75* (2013.01); *G06F 8/751* (2013.01); *G06F 19/22* (2013.01); *G06F 21/563* (2013.01); *G06F 21/64* (2013.01)

(58) Field of Classification Search
CPC ........................................................ G06F 8/53
USPC ........................................................ 717/143
See application file for complete search history.

(56) References Cited

U.S. PATENT DOCUMENTS

| | | | |
|---|---|---|---|
| 6,374,242 B1 * | 4/2002 | Childs | G06F 17/2294 |
| 7,698,558 B2 * | 4/2010 | Tomkow | H04L 51/30 709/206 |
| 7,702,057 B2 * | 4/2010 | Sidiropoulos | G06F 1/10 375/371 |
| 7,814,107 B1 | 10/2010 | Thirumalai et al. | |

(Continued)

OTHER PUBLICATIONS

Hindawi Bio Med REsearch International, "Improving the Mapping of Smith-Waterman Sequence Database Searches onto CUDA Enabled GPUs", Jan. 2015, pp. 1-8, ]online][retrieved on Jan. 29, 2018]. Retrieved from <https://www.hindawi.com/journals/bmri/2015/185179/>.*

(Continued)

*Primary Examiner* — Evral E Bodden
(74) *Attorney, Agent, or Firm* — Haverstock & Owens LLP

(57) ABSTRACT

In a dynamic computing environment, it is a nontrivial task to verify code running in the environment because most approaches to software similarity require extensive and time-consuming analysis of a binary, or the approaches fail to recognize executables that are similar but nonidentical. A biosequence-based method for quantifying similarity of executable binaries is used to identify allowed codes in a real-world multi-user environment.

30 Claims, 5 Drawing Sheets

(56) References Cited

U.S. PATENT DOCUMENTS

| | | | |
|---|---|---|---|
| 8,347,214 B2* | 1/2013 | Dillon | G06F 9/541 |
| | | | 715/744 |
| 8,494,985 B1* | 7/2013 | Keralapura | H04L 63/0245 |
| | | | 706/12 |
| 8,661,405 B2* | 2/2014 | Stevenson | G06F 8/20 |
| | | | 717/105 |
| 8,881,122 B1* | 11/2014 | Klimek | G06F 8/436 |
| | | | 717/140 |
| 2001/0053957 A1* | 12/2001 | Blair | G06F 17/30982 |
| | | | 702/19 |
| 2003/0054407 A1 | 3/2003 | Luo | |
| 2004/0034846 A1* | 2/2004 | Ortal | G06F 8/24 |
| | | | 717/111 |
| 2004/0221270 A1 | 11/2004 | Witchel | |
| 2008/0077570 A1* | 3/2008 | Tang | G06F 17/30684 |
| 2009/0235054 A1 | 9/2009 | Pan | |
| 2009/0313271 A1* | 12/2009 | Zeidman | G06F 8/71 |
| 2010/0281540 A1 | 11/2010 | Alme | |
| 2012/0246654 A1 | 9/2012 | Eichenberger et al. | |
| 2014/0195474 A1 | 7/2014 | Anguera Miro | |

OTHER PUBLICATIONS

Cesare. "Software Similarity and Classification." Jun. 2013 Retrieved from <http://dro.deakin.edu.au/eserv/DU:30063491/cesare-softwaresimilarity-2013A.pdf>, entire document, pp. 35.

* cited by examiner

BIOSEQUENCE-BASED APPROACH TO ANALYZING BINARIES

CROSS-REFERENCE TO RELATED APPLICATION(S)

This application claims priority under 35 U.S.C. § 119(e) of the U.S. Provisional Patent Application Ser. No. 62/149,126, filed Apr. 17, 2015 and titled, "What's Really Running on Your Cluster: A Biosequence-Based Approach to White-listing HPC Applications in a Development Environment," which is hereby incorporated by reference in its entirety for all purposes.

U.S. GOVERNMENT AGENCY AND THE GOVERNMENT CONTRACT

The invention was partially funded by an agency of the United State Government or under a contract with an agency of the United State Government. The name of the U.S. Government agency and the Government contract number are: Laboratory Directed Research and Development (LDRD) at Pacific Northwest National Laboratory (PNNL) via the Data Intensive Computing Initiative (DICI), Information and Infrastructure Integrity Initiative (14), and Signature Discovery Initiative (SDI). Pacific Northwest National Laboratory PNNL is operated for the DOE by Battelle under contract DE-AC06-76RL0-1 830.

FIELD OF THE INVENTION

The present invention relates to the field of computer analysis. More specifically, the present invention relates to software identity verification.

BACKGROUND OF THE INVENTION

For many multiuser environments such as High Performance Computing (HPC) centers and cloud platforms, there is an increasing security-related need to know how those resources are being used. From preventing inefficient use of a capability to detecting unwanted or illegal codes, there is a spectrum of desired and undesired code that system maintainers should be cognizant of. The science of reliably developing and identifying signatures for diverse cyber datasets such as an executable software corpus is increasingly challenged by the rate, volume, and complexity of software that is available. New applications are coming online at an increasing rate as computation capabilities, network bandwidth, and compute cycles continue to increase according to Moore's Law. In particular, the challenge of software identity verification, or identifying what binaries are executing on a system at a given time is increasingly difficult as the number and complexity of applications continues to increase, as well as the number of variants of any given application. A binary is a file or code. Some binaries are functional without an installer.

Clone detection is an existing software analysis approach that could potentially be used to recognize highly similar variants of a binary family. Applications of clone detection are generally applied to large-scale code base software for the purpose of 1) finding and eliminating cut-and-paste segments in a large software projects because these are especially prone to introduce complexity and bugs, 2) identifying instances of software plagiarism, or 3) for making sure licensed code is free of open source code fragments or other software that would jeopardize a commercial license. Clone detection is typically done either by analyzing source code, or by operating on the disassembled binary (e.g., the assembly instructions).

Detecting similar binaries directly is the target of many commercial offerings and research projects, most of which are based on code signatures. Typically these signatures are built from checksums or other transformations of the binary sequence into numerical representations where finding a match is equivalent to finding equal checksums. There are many variations on this theme including simplistic approaches where a single checksum is calculated for each binary. Such exact-matching methods are not suitable for recognizing binaries in a development environment, as the binaries should not be exact matches. Likewise in cloud environments, there may be so many (near identical) variants that exhaustively characterizing them beforehand is not practical. Exact-match based approaches fail because by adding a single nonsense instruction or changing a single data field (such as an internal author name or timestamp) results in an entirely unrelated checksum value. This is because in general checksums do not preserve similarity.

The main limitation of hash-based methods is that because hashing determines an exact match or no match (instead of a near match) for the segment being hashed, they have an inherent tradeoff between sensitivity and specificity. A hash of an entire binary will only match another binary if they are exact matches. Introducing a single meaningless instruction into one binary will change its hash, making it appear as an entirely distinct artifact. Hashing instead at the section level for the same example would produce a series of hashes that are the same and one that is different. However, a single trivial addition to each section would make all of them look distinct, again confounding the method. At the other end of the spectrum, graph similarity approaches are either computationally costly (and therefore not practical solutions for line-speed identification of clones), or sensitivity is sacrificed for speed.

SUMMARY OF THE INVENTION

In a dynamic computing environment, it is a nontrivial task to verify code running in the environment because most approaches to software similarity require extensive and time-consuming analysis of a binary, or the approaches fail to recognize executables that are similar but nonidentical. A biosequence-based method for quantifying similarity of executable binaries is used to identify allowed codes in a real-world multi-user environment.

DETAILED DESCRIPTION OF THE PREFERRED EMBODIMENT

Figures 1, 2:
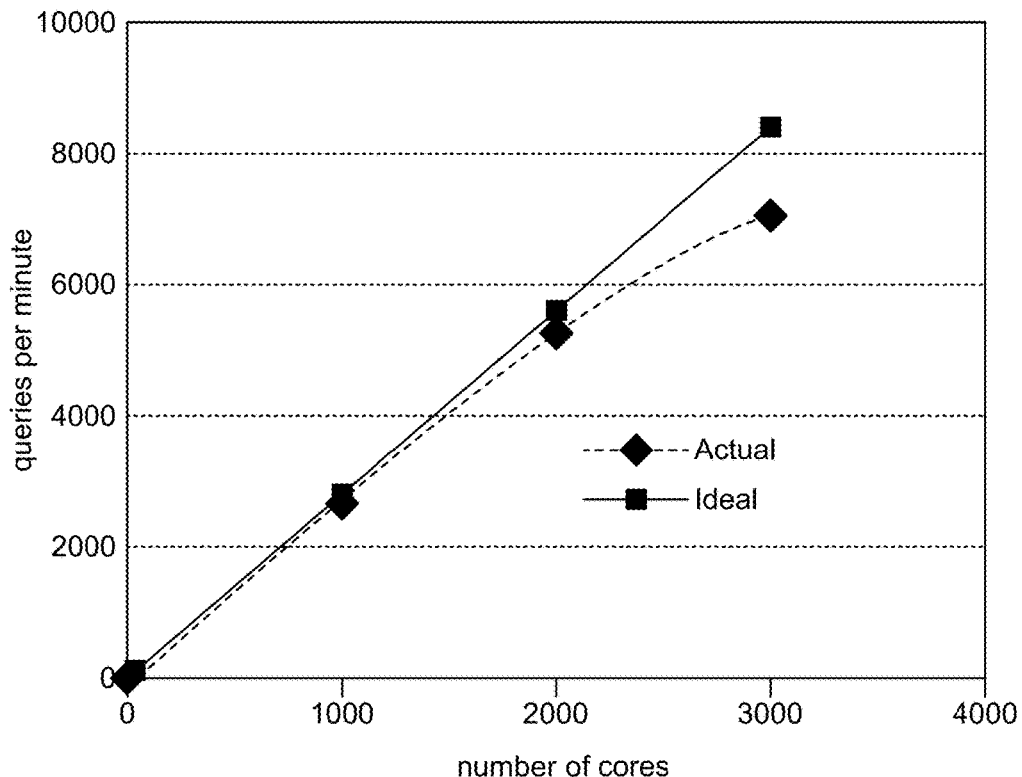
FIG. 1 shows alignment of a protein representation of software according to some embodiments.
FIG. 2 illustrates the scaling performance of MADBlast according to some embodiments.

An organic variation in the population of binaries motivates an approach for recognizing "families and variants" of software binaries as opposed to "individuals." The ability to recognize related but distinct variants is important for several practical applications, such as maintaining a large repository of software (such as the NIST repository) in which one would not want many redundant copies of closely related binaries, detecting the presence of freeware or other licensed code within a developing codebase, and ensuring that only certain applications are used in restricted environments (whitelisting), to name a few. For such applications, instead of traditional code analysis, which may require extensive computational power and far more detailed analysis than necessary, there is a need to draw from techniques in other domains such as biological sciences that are more amenable to recognizing families and variants.

Described herein is a novel bio-inspired method for recognizing similar software. This method is demonstrated to be a suitable algorithm core for the problem of executable binary whitelisting via verifying software identity against known examples of the software. In active environments, many slight variants of software may exist. It is unreasonable to expect that each executing individual is an exact match to any previously reported software individual. So biosequence analysis is an ideal technique to quantify the extent to which the new software matches a sequence-based model of software.

For software identity verification, a collection of software variants from the same code family is thought of as a "species" and each time a user wants to execute a code, that "individual" is checked to make sure it is truly a member of the species. As a simple example, the collection of Windows® Notepad applications is a species, and each individual LINPACK executable binary is one individual. LINPACK is a different species than the computational chemistry code NWChem. LINPACK versions 1.2 and 2.3 are different individuals within the same species. If a user of a multi-user platform wanted to run LINPACK using a batch submit script, the process of software identity verification would analyze the binary before allowing the job to run to ensure that the executable being submitted is, in fact, a member of the LINPACK family by comparing to known LINPACK family members.

Since the software in multi-user environments is highly dynamic, it cannot be expected that each executing individual is an exact match to any previously seen software individual. In addition, it is impractical to maintain a list of all possible variants and to check the new request against the entire list. So instead, biosequence analysis is used as a way to quantify the extent to which the new software matches the sequence model for the rest of the family. If the software request passes the test, it would be allowed to run on the HPC platform.

Described herein, instructions are resolved and exact matches are made more flexible by allowing insertions or mismatches that occur under a threshold. In more sophisticated approaches, disassembly is used as a preprocessing step to identify code segments such as functions that generate check-sum signatures. This is a very promising approach and has been shown to eliminate many duplicates or near duplicates from a corpus of known malicious software. Other variants use techniques such as using disassembly to identify the entry point of a binary as the starting point for an assembly stream signature. Though signatures do allow for some flexibility in binary recognition, a method is needed to "discover" the most reliable indicators of particular code families.

Taking this one step further, it has been shown that highly similar regions of a binary are able to be identified using disassembled, normalized sequences combined with locality sensitive hashing (a relaxed form of locality preserving hashing). Including dynamic analysis with normalized instruction sequences has been shown to increase sensitivity when program behaviors are correlated with static analysis.

Herein, two methods are described: instruction frequency vector and bioinformatics-based similarity analysis. These are two approaches for software identity verification are demonstrated to surpass the limitation of hash-based approaches (which would trivially fail to identify any similar but non-identical software artifacts). The bioinformatics-based approach has been demonstrated as a powerful tool when operating on Abstract Syntax Trees (AST). The method described herein uses a similar approach, but instead of using the AST, it only relies on disassembly of a binary. These methods do not rely on presence of source code, nor do they analyze complex lexical features or structures within the binaries and so operate on raw binaries quickly. They rely only on analysis of disassembled instructions. The motivation and features of these two approaches are described in greater detail in the following sections.

Instruction Frequency Vector Similarity

Instruction frequency vector-based similarity analysis tests the degree to which a global, frequency-based representation of a software binary's disassembled instructions is able to detect similar software instances, even when those binaries are nonidentical. Vectorization is a "global" approach in that a single feature vector describes an entire code instance and therefore would be most useful in identifying when one entire instance is similar to another entire instance. This method would not be useful in detecting the similarity of individual parts. For the application of software identification verification, this whole code approach may be reasonable in many cases because one seeks to answer the question "is there enough evidence that a test binary is indeed a member of a predetermined binary family?" Global binary similarity methods such as this are not expected to work as well in large or highly variant families or subfamilies, but represent a simplistic starting point for rapid software identification verification and is included for comparison. Feature vector approaches make a simplifying assumption that the order of instructions is not important in distinguishing between binary families. As a consequence, feature vector-based approaches are computationally simpler than more complex analysis (such as bioinformatics-based), but are not expected to have the same statistical performance in identifying members of highly variant binary families.

Bioinformatics-Based Similarity

Biosequence analysis provides an alternative to the limitations of hash-based and graph-based methods for binary analysis. Biosequences are chemical chains from a fixed number of subunits (4 subunit types for DNA and RNA, and 20 subunit types for proteins). Since DNA is inherited and modified from one generation to the next, similarities in DNA sequence (or in protein sequence which is related to DNA sequence) appear in organisms that share ancestors. Computational methods for discovering sequence similarity in biosequences have been developed and refined for decades. These methods are variations on dynamic programming approaches to map strings that represent biomolecules onto one another—a process called alignment. Alignment also results in a similarity score that can be used as a proximity metric.

The bioinformatics-based method described herein is based on the computational algorithm BLAST, which is a statistical method for comparing text strings that represent biological chemical subunits. In BLAST, performing string alignment finds regions of commonality that exceed a statistical expectation, and is highly tolerant to mismatches, insertions and deletions. BLAST applied to binary analysis is attractive because it tolerates a high degree of dissimilarity and has the ability to identify sub-regions of binaries that are highly similar. String matching in BLAST is much more flexible than regular expressions, edit distance, or other traditional computational methods. BLAST compares a test string against a collection of reference strings to quantify the extent to which the test string is believed to be related to the reference strings. This is reported as a score and a statistical confidence measure for each test/reference pair having a score that beats a user-defined threshold. The calculated alignment between the strings is also reported. FIG. 1 illustrates how an alignment between two strings is reported in BLAST.

FIG. 1 shows alignment of a protein representation of software. The top panels are the string representations of two code individuals, and the bottom panel shows the alignment between them. Dashes indicate places where one code contains inserted instructions not found in the other code. Bold characters denote mismatches between the individuals that are in the alignment region.

Since BLAST does not operate on a higher-level structure, it does not incur the overhead of determining abstract syntax tree (AST) or program dependence graph (PDG) information from a binary, but has the potential to be more specific than frequency-based feature vector representations of code because key patterns in the sequence of instructions are preserved.

The approach is to map the challenge of software identity verification into a sequence analysis problem by breaking up the analysis into two phases. In the first phase, members of a software family are disassembled and converted to sequences and analyzed using a high performance implementation of sequence analysis software. The high performance sequence analysis software, known as MADBlast, is a multiprocessor implementation of the BLAST sequence alignment method. MADBlast allows for a more generalized alphabet, and more efficient monitoring of node utilization during task execution. In the second phase, a model of a code class (software species) is constructed for the purposes of comparing to new requests for executing code on a multi-user system. Comparing a submitted executable to a library of acceptable code models in this second phase does not require HPC, and is able to execute very rapidly on management nodes to provide some assurance of the code a user is requesting to run.

In BLAST, the most notable of these methods, string alignment finds regions of commonality that exceed a statistical expectation, and is highly tolerant to mismatches, insertions and deletions. BLAST applied to binary analysis is an attractive alternative to hash-based methods because it tolerates a high degree of dissimilarity. Similarly, because BLAST does not operate on higher-level structure, it does not incur the overhead of getting AST or PDG information from disassembly, but has the potential to be more specific than vector representations of code because some notion of the sequence of instructions is preserved. MADBlast enables running massively parallel BLAST calculations on very large datasets in phase I, where the model for the binary family is generated. MADBlast also allows for very rapid comparison of a test (unknown) binary to a library of known family models in serial mode.

Software, including code under development, is organic in nature. There is inheritance, sharing, specialization, and mutation between generations of code, and optimization to efficiently utilize finite resources. By using BLAST as the basis for quantifying binary similarity, organic models are used as measures of code similarity. In doing this, precise understanding of what the code is doing is lost, but the ability to see similarity across a large corpus of software binaries is gained. Though BLAST analysis is not used to say definitively what the code is doing, this method is still able to be used to organize large datasets into meaningful families to discover signatures and make predictions about the family membership of previously unknown individuals.

The clone detection problem is mapped to a string alignment problem by disassembling binaries of interest including functional block information when it is available. Functional blocks within code are similar to proteins within a species. A single species will have many proteins, just as a single binary will have multiple functional blocks. Also, string alignment works best when done using a small alphabet (tens of characters to express thousands of instruction types), so rather than treating all the instruction/argument combinations separately and looking for similarities (which is how conventional string matching is usually done on disassembled binaries), the method coalesces many instructions performing similar tasks into topical categories and ignores arguments. This has the effect of generalizing the instruction stream. Similar to the tokenization methods, this generalization operates at the assembly level. 'Tokenizing' at the assembly level is done by grouping like types of instructions, and for the same reason that variable names are dismissed in tokenization of source code, details of the instruction are normalized out and the further step of ignoring the arguments (other than potentially as a source of error detection in the disassembly) is taken.

This is a significant deviation from most clone detection methods because all of the syntactic and structural information from the original binaries is intentionally not kept. Instead, the clone detection problem is turned on its head, and the question is asked, "Are there highly conserved patterns between these two binary streams that are more likely than would be expected by chance?" The answer to this question yields information about commonalities that may be meaningful within software families and signatures of these families. Sequence analysis for binaries lends itself directly to these types of analysis because they are well-studied problems for protein systems. This is where the mapping from binary analysis to protein sequence analysis provides value—automatically obtaining phylogenetic and family-based analysis techniques and motif-finding capabilities as a consequence of using mature bioinformatics approaches.

Converting Executable Binaries and Normalization

Converting binaries to string representation begins with disassembly. In general the process of disassembly converts an executable binary into functional blocks of assembly instructions with their associated arguments. For example, a single addition operation in source code would be converted to a pair of "mov" operations to retrieve values from memory and place them in an arithmetic unit, a second operation to "add" the values, and another "mov" operation to place the result of the add operation into a new location in memory.

In some embodiments, the disassembly method is based on a GNU GPL licensed project named Objconv written by Dr. Agner Fog from Copenhagen University, that is distributed with most Linux operating systems. Objconv provides an excellent balance of accurate disassembly and speed. To automate the disassembly process into creation of files properly formatted for sequence analysis, Objconv has been extended with an application called Distfast, which is a wrapper in either C++ or Python that allows control of inputs to and to process outputs from Objconv. Distfast also provides the conversion of Objconv output to a protein representation using the tokenization mentioned above. This format is called FASTA format (the format on which BLAST analysis is able to be directly applied), eliminating the need to post process files for alignment analysis.

This modified disassembler was applied to binaries of interest, resulting in assembly sequences broken into functional blocks for each binary. Assembly sequences were normalized by removing all the arguments and grouping similar opcodes categorically, mapping each category to a single letter. This mapping captures the vast majority of commonly occurring instructions with the exception of no-op.

Two types of normalization occurred to develop the mapping from raw binaries to frequency vector or biosequence representations. The first normalization step was to discard all arguments to the assembly instructions. The second normalization step filtered out both highly frequent and very infrequently occurring instructions. The top frequently occurring instructions were ignored as they occur so frequently they would dominate any representation of the binaries. This resulted in 27 groups of instructions that covered the majority of instructions in the corpus by occurrence. All of the remaining less-frequently occurring instructions were ignored. This filtering step is done to maximize the information content of both the vector and biosequence binary forms by not reserving space or characters for highly infrequent instructions.

Instruction Frequency Vector Method

Each normalized binary sequence was represented as a feature vector having 27 elements, the value of each element being the relative abundance of a particular instruction in the binary. This obscured any effect that length of the binary might have. To generate a distance measure between the $i^{th}$ and $j^{th}$ binaries, the Euclidean distance ($D_{ij}$) between their frequency vectors was calculated. Since the vectors were normalized to the positive hypersphere, a simple similarity measure of $1-D_{ij}$ was calculated between all pairs of binaries.

Bioinformatics-Based Similarity Method

Applying biological sequence analysis to software binaries is a several step process. Instruction sequences are filtered as described above and binaries are transformed into the protein representation to be used by the BLAST algorithm implemented in the MADBlast tool. MADBlast is used to perform sequence alignment to find related subsequences. MADBlast takes as input text strings, a scoring matrix that contains reward values for text alignment and misalignment events, and scoring parameters such as the gap opening and gap extension penalties. This method has been generalized in prior work to be applicable to string alphabets beyond just the standard 20 amino acid characters expected by biological BLAST codes. A scoring matrix that is specific for binary analysis is utilized. Each of these steps is described in more detail herein.

Generating Similarity Scores for Sequences

MADBlast is used to compare each of the sequences disassembled from a corpus of HPC binaries to each of the other sequences from this corpus. This produces a BLAST output file with a record of the sequences that significantly aligns with each functional block from each binary with all of the functions from all of the other binaries in the corpus. The resulting MADBlast scores are the basis for using individual sequences as binary models to discover other similar binaries. These scores are also used as distance measures for family tree analysis using the hierarchical clustering tool WEKA with Euclidean distance as the distance measure.

Two different stringency levels were tested for a positive "hit" between sequences. A less stringent cutoff is defined by sequences sharing an alignment of at least 10 characters with at least 50% identity (Len 10, Id 50%). A more stringent cutoff is defined when a pair has a BLAST alignment of length 50 with 80% identity or better (Len 50, Id 80%). These scores are chosen based on previous experience with MADBlast, and multiple scores are chosen to avoid sensitivity to any one set of cutoffs. Because the BLAST algorithm masks low complexity sequences, many functions do not match even themselves. Failure to self-match is used as a functional filter to eliminate sequences that exhibit low complexity.

Binaries are composed of many functions, each treated as individual sequences. To aggregate the results of function-level similarity to a score of similarity of two binaries, denoted as A and B herein, results are reported as a fraction where the denominator is the number of sequences for binary A that had any alignment above the chosen stringency level. The numerator for each similarity is the number of sequences in A that matched any function in B at the given stringency level. A perfect score of 1.0 indicates that all of the functions that had any alignment matched A to B. A poor score of 0.5 means that only ½ of the functions from A matched a sequence in B, and ½ matched other targets.

Reimplementing Serial BLAST

In processing very large high performance codes, it is found that functional blocks that are extremely long and some that are extremely short are obtained. Very short sequences do not have enough information to reliably determine whether their similarity to another sequence is random or not, so sequences shorter than 10 characters after translation are eliminated. Very long sequences are handled specially within the MADBlast code by breaking them into multiple subsequences of a fixed length.

The BLAST algorithm was originally published in 1990 and with its related papers has been cited over 100,000 times for use in applied research such as drug discovery and biomarkers research, and decades of fundamental research into molecular processes that give species and communities the capacity to survive. In fact, typical sequencing platforms that are mostly responsible for the influx of new sequences to analyze are increasing their throughput more quickly than Moore's Law—leading to a situation in which the need for computing is outpacing the underlying hardware improvements. This motivated a need for parallel implementations of BLAST such as ScalaBLAST. However, BLAST was not implemented as a library, so using it as the algorithmic core of ScalaBLAST and other parallel implementations is challenging because of its lack of external API and problematic because of the possibility of unintentional side effects when modifying the BLAST core. As with most scientific software, the low-level details of how BLAST is implemented have been left out of publications. Even with the large corpus of publications on the details of BLAST, there were many implementation-level details that were discovered to create a repeatable BLAST compute core.

The BLAST functionality to drive protein comparison calculations (the blastp operating mode) has been reimplemented for transparency and understanding of the implementation details, and to avoid introducing unwanted side effects into the serial BLAST core when driving it with a parallel MADBlast control layer. A second motivation for refactoring the BLAST core was to generate a domain-agnostic (e.g., non-biological) string analysis platform.

The memory needed for the Smith-Waterman calculations is allocated once up front and is reused for each alignment. The size of memory allocated is determined via options to the program. This provides increased speed and prevents many memory-based errors and issues. In standard versions of BLAST, large sequences are not handled well—they are not common in nature but are very common in binary analysis. Large sequences are split, based on the amount of memory available and processed in pieces. MADBlast does the work needed to output the alignments correctly even when they have been split.

As mentioned above, BLAST is based on biology and therefore only allowed for 20 "letters" (amino acids). This number was too constraining for binary analysis so MADBlast is able to take in an arbitrary alphabet. In some embodiments, any printable ASCII character (except for > and # which are used as part of the input files) are allowed. The algorithms and heuristics have been modified to account for an arbitrary alphabet.

The background frequencies for the alphabet are specified in a scoring matrix which are usually hard-coded into the BLAST implementation. MADBlast allows for plug and play of new scoring matrices based on the alphabets chosen. There are a few other "tuning" variables that are configurable and no longer hard coded.

These changes enable removing the biology and chemistry from the BLAST algorithm and making alignments based on the domain of the proteins such as binary code.

The ability to run large data through MADBlast quickly and its ability to understand binary-based proteins is important.

MADBlast uses ZeroMQ (REF) for interprocess communication and uses Slurm libraries when run in clustered mode. At its core is a single processor implementation (multi-threaded) of the BLAST algorithm (SerialBlast) which is able to be run on its own. MADBlast does not rely on any external libraries. In "clustered" mode, a ZeroMQ layer wraps SerialBlast directly. Each core receives tasks and uses its SerialBlast core to perform the alignments.

MADBlast is built using a master/workers/tasks concept. There is one master process per job and all the other cores are workers. Tasks are handed out by the master to worker cores. The master reads through the query FASTA file (set of proteins to be compared) and hands out tasks when requested.

At startup, the master opens the query FASTA file and waits for requests. Workers allocate enough memory to run local Smith-Waterman calculations. Each core on a node allocates memory one at a time. If there is not enough memory left, cores that come online later will not allocate memory or run—therefore running cores are always guaranteed to have enough memory to complete their BLAST calculations. As soon as a core allocates its memory, it requests a task from the master—it does not have to wait for the rest of the cores to get their memory. Allocating memory up front once avoids constant allocate/destroy calls. Running out of memory on a machine is avoided since throughput is reduced to stay within the memory constraints. Each node is able to allocate a different amount of cores/memory. If the nodes in a particular cluster or job have different amounts of RAM, then planning for a lowest common amount is not necessary.

A problem was encountered with this approach when a database (the list of things being compared to) is extremely large and a query is extremely long. Long queries will keep searching through the large database for long times after all the other queries have finished processing. For example, in one case 97% of the queries were finished in 20 minutes but the last 3% of queries took over 2 hours.

A solution was developed that is ubiquitous and will detect the problem and mitigate it in code. If a worker core has been processing the same query for longer than 30 seconds, it will ask the master for help. The master may respond with "no" because all the cores are still busy, so the task will keep working and then ask again in another 30 seconds if it still has not finished. It will continue to do this until it gets a "yes" or is done. When the master has some resources available it will divide up the remaining portion of the database that the worker was unable to search, and hand out that work to idle workers. The worker that requested help waits for responses from the workers with their results. The original worker will then combine the results and finish normally. The scaling performance of MADBlast is illustrated in FIG. 2.

To ensure that biological assumptions are not being imposed on non-biological datasets, and to enhance reuse of the BLAST algorithmic core, a BLAST implementation is developed that is free of biological assumptions called MADBlast. Both the algorithmic redesign and the parallel driver that accompanies it are described below.

BLAST supports many different modes of running (e.g. DNA vs. DNA comparisons and protein vs. protein comparisons). But for the purposes of analyzing executable binaries, the only functionality required was the ability to compare protein sequences—the blastp operating mode. Several code features are important for this refactored BLAST implementation:

Memory is allocated for the dynamic programming calculations (key alignment algorithm) once up front and reused for each alignment.

Large sequences are split, based on the amount of memory available and processed in pieces and reassembled as needed.

Arbitrary alphabets up to about 80 characters are supported, using standard ASCII characters, with several restrictions caused by file format constraints.

User-specified scoring matrices are selected at run-time, as well as a few other "tuning" variables that are now easily configurable and no longer hard-coded.

Making Serial BLAST Parallel

A key feature of MADBlast that enables the analysis described herein is parallelization using ZeroMQ. This allows large corpuses of binaries to be analyzed quickly using a cluster. Note that this is only important when performing the initial similarity score generation. During normal operation a single core is sufficient to compare unknown binaries to groups of known binaries.

Data

The binaries used in the example application of this binary similarity method come from the Pacific Northwest National Laboratory Molecular Science Computing Facility, a production computing HPC center that focuses on environmental and molecular science calculations. This center supports many users who develop and run a variety of computational chemistry and other codes. To simulate a whitelisting application, a sample of the executable binaries compiled for this system was obtained and analyzed to quantify the extent to which binaries known to be similar were found to be similar using the two methods described. This collection of binaries had 5 different computational chemistry codes, each having a different number of variants, and one instance of a bioinformatics application. The largest family was the computational chemistry package, Amsterdam Density Functional (ADF), having 22 different versions on the system. ADF is used as the family of interest in this study, and treat other codes as "out groups," such as Amber, CP2K, VASP, Lammps and ScalaBLAST. Table 1 contains the disassembly times and number of families in each family.

TABLE 1

Code Species Disassembly Times

| Code Species | # Variants | Mean Disassembly Time (mins) | Code Type |
|---|---|---|---|
| ADF | 22 | 136 +/− 252 | Chemistry |
| Amber | 8 | 14.0 +/− 7.7 | Chemistry |
| CP2K | 3 | 350 +/− 334 | Chemistry |
| VASP | 2 | 32 | Chemistry |
| Lammps | 2 | 13.5 | Chemistry |
| ScalaBLAST | 1 | 11 | Biology |

After disassembly, there were 520,060 functional blocks across the code corpus represented as distinct biosequences.

For Phase I, MADBlast was used to compare each of the sequences in this list to each of the other sequences on the list. This produced a BLAST output file with a record of the sequences that significantly aligned with each functional block from each binary individual with all of the functions from all of the other binaries.

These scores were used to calculate the degree of similarity between all pairs of binaries, as described below. Similarity scores were used to assess the ability of each member of a family (or subfamily) to correctly identify other members of the family (or subfamily). These scores were also used in family tree analysis using the hierarchical clustering tool WEKA with Euclidean distance.

For Phase II analysis, two different definitions of a positive "hit" between sequences were used. A less stringent definition was when sequences shared an alignment of at least 10 characters with at least 50% identity (Len 10, 50%). The more stringent definition was when a pair had a BLAST alignment of length 50 with 80% identity or better (Len 50, 80%). Because BLAST masks low complexity sequences, many functions did not match even themselves. This is used as a functional filter to eliminate sequences that exhibit low complexity. Table 2 contains the number of sequences that remained in this dataset using various pre-BLAST length filters (# Seq.), the number that exhibited enough complexity to be aligned (# Cplx), and the numbers of sequences that had any alignment at either the less or more stringent alignment levels.

TABLE 2

Alignments from Sequences of Varying Lengths

| Pre-BLAST cutoff | # Seq. | # complex | Len 10 50% | Len 50 80% |
|---|---|---|---|---|
| 10 | 377907 | 129999 | 129060 | 68887 |
| 50 | 204557 | 112637 | 111976 | 69218 |
| 100 | 153110 | 99559 | 98955 | 64521 |

Assessing Statistical Performance

As described herein, results reported herein for degree of similarity between binary individuals are a fraction where the denominator is the number of the sequences for a given query binary that had any alignment of the particular stringency level. The numerator for each similarity is the number of sequences in the query binary that matched any function in the target binary at the given stringency level.

Statistical performance of the method was calculated using a Receiver Operator Characteristic (ROC) on the ranked percent similarity scores between all pairs of binaries. This is equivalent to using a single member of a family as a classifier to identify the whole family, and the ROC is perfect (e.g., has an area under the curve (AUC) of 1.0) if the query as well as all of the other family members have higher percent similarity than all of the non-family members. Because the ROC relies only on relative ranking of test subjects, the threshold score is also reported, which is the percent similarity score required to correctly identify 90% of the true family members. Ideally this would be close to 100%, so that a stringent cutoff could be used to identify other family members on a given system, but not exactly 100% because some differences between family members are expected.

Using each binary as a classifier, the ROC, which is a plot of true positive vs. false negative as similarity cutoff varies from 1 to 0, was calculated by sorting the similarity scores for that binary against all binaries in a test set. Area under the ROC curve was used as a measure of statistical performance, with 1.0 being a perfect score. The similarity threshold required to correctly identify 90% of the true members of a family ($T_{90}$) was calculated by using the sorted similarity list for each binary and locating the similarity value at which at least 90% of true positives had been identified. Because ADF was the largest code family, having 22 different members, ADF was treated as the positive group, and all non-ADF instances were treated as the negative group.

Statistical significance of AUC and $T_{90}$ results for feature vector and bio-based techniques were tested using one-way analysis of variance (ANOVA) to identify which families and subfamilies had statistical performance differences. For families or subfamilies determined by ANOVA to have statistically significant differences, Tukey's honest significant difference (HSD) method was used to identify which technique pairs produced the statistically significant differences. For both ANOVA and Tukey's HSD test, a significance value of 0.05 was used.

Results

Figure 3:
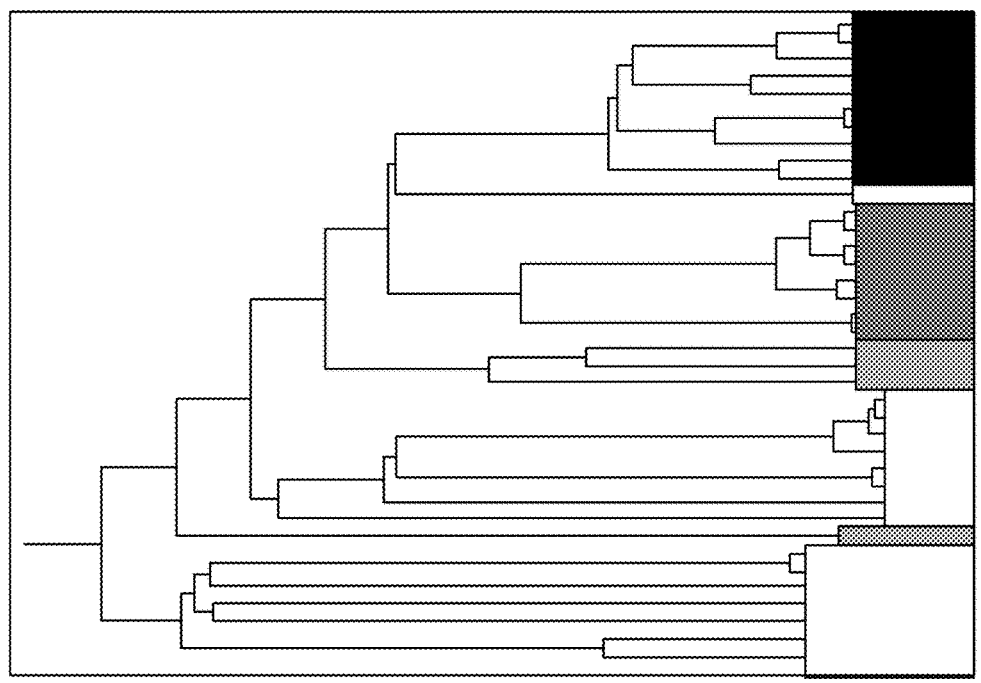
FIG. 3 illustrates the results of a family tree with all ADF family members in grey or black, and all non-ADF individuals in white according to some embodiments.

Applying hierarchical clustering to the MADBlast output revealed that there is a strong family similarity within 3 subgroups of ADF individuals. FIG. 3 illustrates the results of this family tree with all ADF family members in grey or black, and all non-ADF individuals in white. The family denoted in black (arbitrarily identified henceforth as Family 1) had 10 members, nearly half of all the ADF individuals. The family denoted in darker grey (Family 2) had 8 members. The remaining ADF members are shown in light grey.

Black and dark grey are strong subfamilies, each having only ADF instances (ADF family 2 and ADF family 3, respectively). Light grey are outlier ADF instances, and white are non-ADF codes.

This analysis shows that there is strong family resemblance between some ADF individuals using the analysis, but that significant differences exist between some of the subfamilies.

Figure 4:
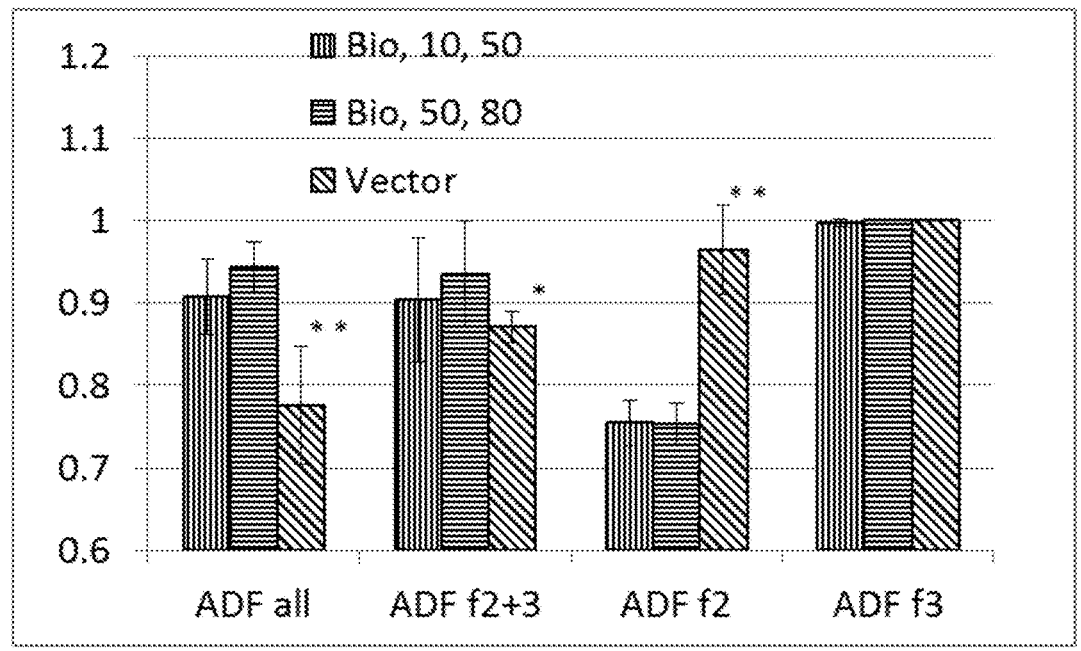
FIG. 4 illustrates the results of Area Under ROC curve according to some embodiments.

Next, the AUC for ROC curves produced by each ADF member were calculated with respect to the full ADF family, and within the combination of subfamilies 1+2, and for subfamily 2 alone. These AUC for each ROC curve are presented in Table 3. Even when all ADF members from disparate subfamilies are combined, the mean AUC for using any member of this family to identify all other members is above 0.9, regardless of whether stringent alignment (10/50/80) or less stringent alignment criteria (10/50/80) are used. But treating this disparate collection of ADF individuals as a family requires a very liberal similarity threshold of 44% to 35% (depending on alignment stringency) to be used on average to correctly identify 90% of the true positives. Ideally, this would be as close as possible to 100% to prevent extraneous similarities from being accepted, but not exactly 100% so that modifications could be tolerated. By contrast, tuning the identification of ADF family members using subfamily structure suggested from FIG. 2 by combining ADF families 1 and 2 and excluding the other ADF members maintains AUC scores and significantly improves the threshold in both alignment regimes to 53% or 47%. Finally, restricting ADF classification to only subfamily 2, the AUC indicates near perfect identification of other subfamily members and the thresholds for correctly identifying 90% of true positives jumps to over 70%.

lies 2 and 3 alone. The AUC for these are illustrated in FIG. 4. FIG. 4 shows mean AUC values for classifying all ADF instances (ADF all), ADF instances from two combined subfamilies (ADF f2+3) and individual subfamilies (ADF f2 and ADF f3) using the vector method, and the bioinformatics-based method with different filtering parameters. Statistically significant difference between vector and one biobased method is indicated by *. Statistically significant difference between vector and both biobased methods is indicated by **.

When all ADF members from disparate subfamilies are combined (ADF all results), the mean AUC for using any member of this family to identify all other members is above 0.9 using the bioinformatics-based method, regardless of whether stringent alignment (Len 50, Id 80) or less stringent alignment criteria (Len 10, Id 50) were used. By comparison, the feature vector based approach yielded a worse performance that is statistically significant when compared to either bio-based stringency classifier. To explore the effects of refining the family definition using the family tree results, the performance of both biosequence-based stringency levels and the feature vector approach were assessed on a combination of ADF family 2 and family 3. This is a more tuned family that does not contain the 4 ADF outliers. The results in FIG. 4 for combining ADF families 2 and 3 (ADF f2+3) show that the stringent bio-based approach performed better than the feature vector based approach at a level achieving statistical significance. However, when the analysis is limited to only ADF family 2 (ADF f2), the feature vector approach statistically outperformed both the biosequence-based stringency levels. When the analysis was restricted to only ADF family 3 (ADF f3), all three methods

TABLE 3

Statistical Performance of Classifying ADF

| Family | AUC 10/10/50 | Thresh 90 | AUC 10/50/80 | Thresh 90 |
| --- | --- | --- | --- | --- |
| All ADF | 0.908 +/− 0.046 | 0.442 +/− 0.223 | 0.943 +/− 0.031 | 0.347 +/− 0.167 |
| ADF family 1 + 2 | 0.904 +/− 0.076 | 0.527 +/− 0.179 | 0.935 +/− 0.065 | 0.472 +/− 0.184 |
| ADF family 2 | 0.998 +/− 0.005 | 0.718 +/− 0.032 | 1.000 +/− 0.000 | 0.753 +/− 0.023 |

The first ADF group is a collection of versions from the year 2013 identified by the software maintainers as "dirac," "adfnbo," "sgf," and "runadf." This group is the outlier ADF group, shown in light gray in FIG. 3 and does not have a strong family substructure. The second group (ADF subfamily 2) has 10 members, each with one or two versions from 2014 and one version from 2013 (labeled as "14", "14*", or "13") and codes identified as "dftb," "band," "nao," and "adf." ADF Family 2 is marked in FIG. 3 with black. The third group, shown in dark gray in FIG. 3 (ADF subfamily 3), contains only versions of ADF from 2014, each with two different instances of "dirac," "adfnbo," "sgf," and "runadf." Both biobased (shown) and vector based (results not shown) family trees yielded identical ADF families 2 and 3, and the same ADF outliers, and all non-ADF codes are outside the ADF subfamily structure. All of the non-ADF codes grouped into correct smaller families with only 2 exceptions—Vasp 4 and 5 are very different according to this analysis, and CP2K 2.4 versions are similar to each other, but very different than CP2K 2.5.

AUC for ROC curves was produced by comparing each ADF member with respect to the full ADF family, and within the combination of subfamilies 2+3, and for subfamiperformed nearly perfectly, and there was no statistically significant difference between them.

Another measure for family classifiers to identify members in a highly varied family is $T_{90}$. In general, a method that identifies most of its family members with a higher degree of similarity may fail to find new distant relatives of an established family. FIG. 4 illustrates the relative $T_{90}$ values for both biosequence-based stringency levels and the feature vector based approach.

Figure 5:
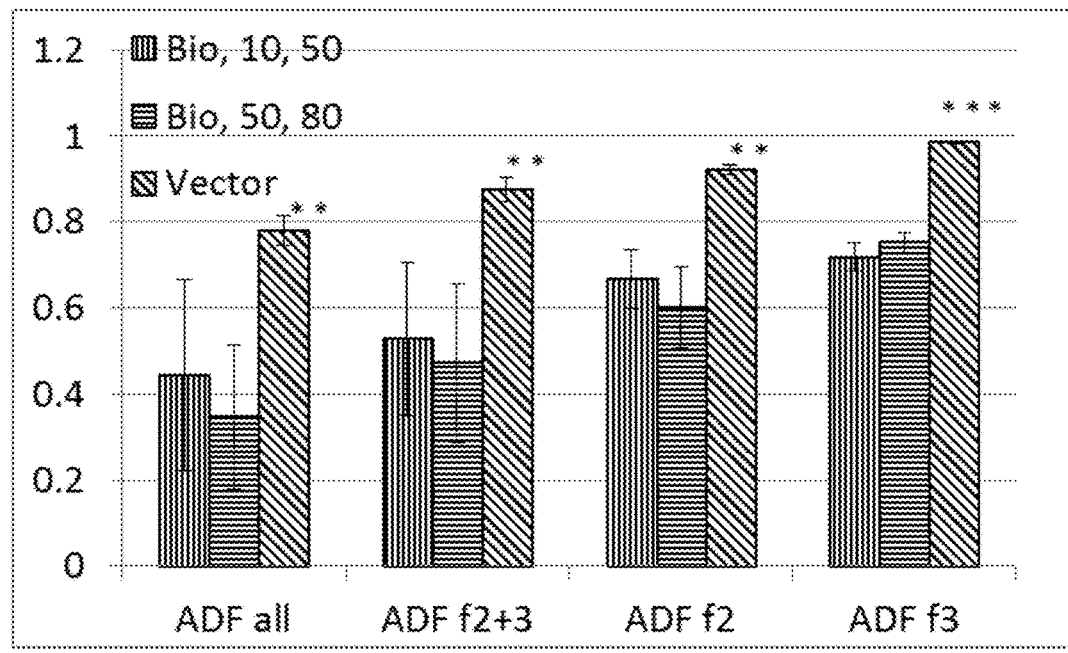
FIG. 5 illustrates the results of Area Under ROC curve according to some embodiments.

FIG. 5 shows mean $T_{90}$ values for classifying all ADF instances (ADF all), ADF instances from two combined subfamilies (ADF f2+3) and individual subfamilies (ADF f2 and ADF f3) using the vector method, and the bioinformatics-based method with different filtering parameters. Statistically significant difference between vector and both biobased methods is indicated by . Statistically significant difference between all three methods is indicated by *.

When identifying all ADF members together, (ADF all, where the biosequence methods both outperformed the feature-vector based method as assessed by AUC), the feature vector $T_{90}$ was statistically significantly higher than that for both the biosequence-based methods. Reducing heterogeneity in the family by excluding the ADF outliers (ADF f2+3) reduced the difference between $T_{90}$ for the feature vector approach and the biosequence-based approach, but the difference was still statistically significant. Considering the next more homogeneous families (ADF f2 and ADF f3), the difference in $T_{90}$ between the feature vector and biosequence-based similarity measures decreased further, but in both cases still achieved statistical significance. It is interpreted that these results suggest that although the feature vector method may sometimes outperform the biosequence-based method for highly tuned subfamilies of binaries, the biosequence-based approach in general is more flexible in identifying members in variant families.

A pair of algorithm designs is described herein for identifying similar binary executables, and these methods are demonstrated in an application of finding similar binaries in multi-user architectures such as HPC centers or cloud platforms. One method is based on feature vectors of disassembled instructions and the other is based on a biosequence-based approach. The feasibility of these methods was demonstrated by applying the methods to the challenge of identifying variants of a computational chemistry code in a collection of real-world software from an operational HPC system that included other chemistry binaries of the same family and from other families as well as a biology code.

This is a significant deviation from most clone detection methods because much of the syntactic and structural information is deliberately ignored from the original binaries. Instead, the clone detection problem is turned on its head to answer, "Are there highly conserved patterns between two binary streams that are more likely than one would expect by chance?" The answer to this question yields information about commonalities that may be meaningful within software families and signatures of these families. Sequence analysis for binaries lends itself directly to these types of analysis because they are well-studied problems for protein systems. This is where the mapping from binary analysis to protein sequence analysis provides value—family-based analysis techniques and motif-finding (a single representation of a family) capabilities are immediately applicable as a consequence of using mature bioinformatics approaches.

Analysis presented herein shows that using the bioinformatics-based method to generate classifiers using known instances of a binary are able to reliably identify many variants of the binary, even when those variants are built with different functionality. Using family tree analysis on the binary family gave insight into subgroups that were treated as subfamilies, and similar classification results were obtained when the subfamilies had members of varying composition.

The three most significant findings are 1) bioinformaticsbased method statistically outperforms the feature-vector-based method when the family of code is larger and more variant; 2) the similarity measure from both the feature vector and biosequence-based approaches yield nearly identical family trees for an example binary corpus; and 3) using the family tree to refine the family definition is able to improve the performance of either the biosequence-based or feature vector-based identification method, in some cases to near-perfect statistical performance.

For the ADF example, the biosequence-based approach is statistically better in the general case when the subfamily structure is not known a priori. When this structure is known, it is possible to tune the performance of some subfamilies, potentially opening the door for a vector-based identification. However, because in the more general case of large, complex code families the biosequence-based approach is more flexible, for many other applications this would be the preferred method.

Using the biosequence-based similarity measure to analyze subfamilies, three interesting partitions were found in the collection of ADF binaries and one orphan variant of ADF existed in the binary collection. A set of code that does not fall into a family is considered an orphan. After talking with the maintainers of ADF on this system, the orphan was identified as an older driver code that was not surprisingly different than the others. The other differences in subfamily composition could be generally explained by differences in code version, or by functionality of the binary versions.

The statistical performance of the biosequence-based method on families and subfamilies is illustrative of the flexible but accurate ability of biological similarity algorithms to recognize familial variants. The described application of identifying similar binaries in a production HIPC environment is just one example of how the method could be used.

The biosequence-based method is able to be used in a variety of other applications including machine utilization measures during run-time. Though this may not be able to block inappropriate binaries from running, it should be able to detect inappropriate utilization of resources. It may be that users are running acceptable binaries in unacceptable ways, resulting in lower overall machine utilization or creating other resource bottlenecks. Characterizing the behavior of software with respect to hardware utilization may provide an alternative to the presented static binary analysis with an analogue of dynamic analysis.

The methods described herein are able to be applied to applications that are most suited for blacklisting. For example, a similar technique might be used for identifying binaries (or binary fragments) that should not be used on a system. In this case the signature is for a functional block, not for an entire binary. The bioinformatics approach is particularly well suited for this application because having models of disallowed binaries would make it possible to identify binaries being used that contain that disallowed functionality, even when it is embedded in a larger, seemingly acceptable application.

Described herein is an example of a novel biosequence-based approach producing a reliable, flexible matching methodology for identifying similar executable binaries. This method was demonstrated on an example of a white-listing application for verifying the identity of executable binaries using data from a live topical HPC system with a corpus of 6 different scientific codes, most having multiple versions on the system. Emphasis was placed on recognizing members of the largest family using other members of the family as an exemplar to assess the ability of this method to operate on highly complex, dynamic codes. For this application, the biosequence method statistically outperformed a simpler feature-vector based method for the binary family under study, and when two of the subfamilies were combined into a single classifier. One subfamily was well recognized by both the biosequence and feature vector methods, and for another subfamily the vector method outperformed the biosequence method. In all cases the threshold score used to detect 90% of the family members was higher (more strict) when using the feature vector based method, suggesting that regardless of false positive rate, the biosequence method was able to correctly find true positives using a more relaxed similarity threshold. Using the HPC implementation of this biosequencebased process, the structure of this family was rapidly learned to guide tuning of the identification process, resulting in a highly accurate and sensitive identification of software family members. Ultimately, this technique could be applied to a wide variety of applications in executable binary characterization and identification.

The analysis shows that using this bioinformatics-based method to generate classifiers using known instances of the code can reliably identify many variants of the code, even when those variants are built with different functionality and optimization levels.

The statistical performance of the method on families and subfamilies is illustrative of the flexible but accurate ability of biological similarity algorithms to recognize familial variants. In practice, a multi-user center could use such analysis to produce a family tree of known acceptable binaries, and select a single member of each subfamily as an exemplar to classify new alleged members of the family. This would provide some measure of reliability that code being run is acceptable, and that it matches user's assertion of what code it is.

Though the method uses disassembly that may take on the order of hours, the method is practical in many batch systems because users often wait that long for a run-time allocation to be granted. In cases where this is not practical, more rapid disassembly techniques are able to be employed, or the method could potentially be combined with a triage phase that uses a simpler but less flexible hash-based approach.

The biosequence approach gives reliable fuzzy-matching methodology for verifying the identity of executable binaries before launch on multi user, multi processor systems. This has been demonstrated using data from a live topical HPC system using 6 different scientific codes, most having multiple versions on the system. Recognizing members of the largest family using other members of the family as an exemplar was a focus. The method was also used to predict key differences in subfamilies of this class of binaries. Using the HPC implementation of this process, this family structure is able to be learned to guide tuning of the identification process, providing a rapid and powerful tool for multi-user systems to verify that only acceptable binaries are being run.

Figure 6:
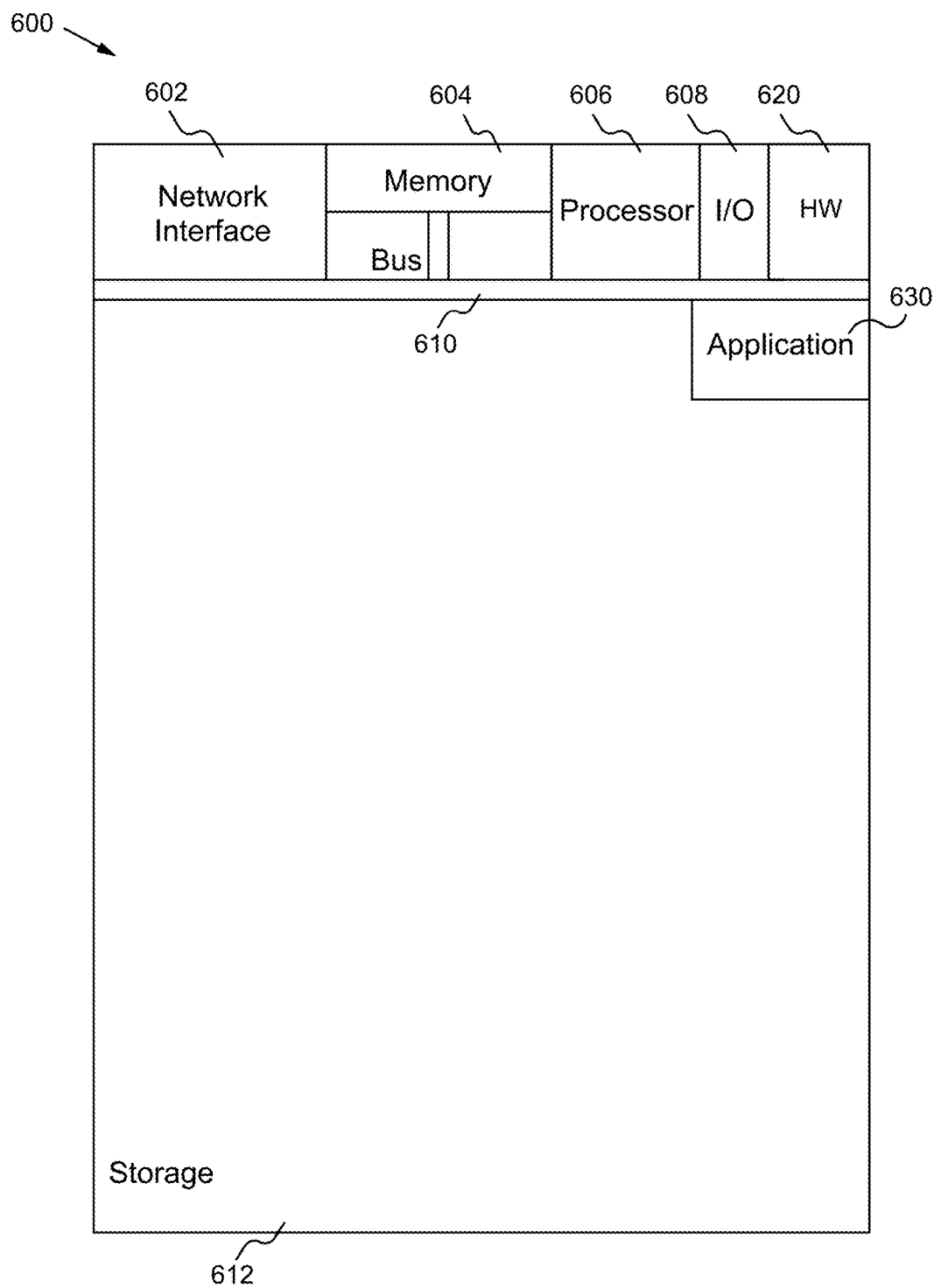
FIG. 6 illustrates a block diagram of an exemplary computing device configured to implement the biosequence-based binary analysis method according to some embodiments.

FIG. 6 illustrates a block diagram of an exemplary computing device configured to implement the biosequence-based binary analysis method according to some embodiments. The computing device 600 is able to be used to acquire, store, compute, process, communicate and/or display information such as binaries. In general, a hardware structure suitable for implementing the computing device 600 includes a network interface 602, a memory 604, a processor 606, I/O device(s) 608, a bus 610 and a storage device 612. The choice of processor is not critical as long as a suitable processor with sufficient speed is chosen. In some embodiments, the computing device 600 includes multiple processors to implement parallel processing. The memory 604 is able to be any conventional computer memory known in the art. The storage device 612 is able to include a hard drive, CDROM, CDRW, DVD, DVDRW, High Definition disc/drive, ultra-HD drive, flash memory card or any other storage device. The computing device 600 is able to include one or more network interfaces 602. An example of a network interface includes a network card connected to an Ethernet or other type of LAN. The I/O device(s) 608 are able to include one or more of the following: keyboard, mouse, monitor, screen, printer, modem, touchscreen, button interface and other devices. Biosequence-based binary analysis application(s) 630 used to perform the biosequence-based binary analysis method are likely to be stored in the storage device 612 and memory 604 and processed as applications are typically processed. More or fewer components shown in FIG. 6 are able to be included in the computing device 600. In some embodiments, biosequence-based binary analysis hardware 620 is included. Although the computing device 600 in FIG. 6 includes applications 630 and hardware 620 for the biosequence-based binary analysis method, the biosequence-based binary analysis method is able to be implemented on a computing device in hardware, firmware, software or any combination thereof. For example, in some embodiments, the biosequence-based binary analysis applications 630 are programmed in a memory and executed using a processor. In another example, in some embodiments, the biosequence-based binary analysis hardware 620 is programmed hardware logic including gates specifically designed to implement the biosequence-based binary analysis method.

In some embodiments, the biosequence-based binary analysis application(s) 630 include several applications and/or modules. In some embodiments, modules include one or more sub-modules as well. In some embodiments, fewer or additional modules are able to be included.

Examples of suitable computing devices include a high performance computing system, a personal computer, a laptop computer, a computer workstation, a server, a mainframe computer, a handheld computer, a personal digital assistant, a cellular/mobile telephone, a smart appliance, a gaming console, a digital camera, a digital camcorder, a camera phone, a smart phone, a portable music player, a tablet computer, a mobile device, a video player, a video disc writer/player (e.g., DVD writer/player, high definition disc writer/player, ultra high definition disc writer/player), a television, an augmented reality device, a virtual reality device, a home entertainment system, smart jewelry (e.g., smart watch) or any other suitable computing device.

In some embodiments, the biosequence-based binary analysis method is implemented using networked devices (e.g., cloud computing). For example, multiple servers perform the biosequence-based binary analysis method is implemented.

Figure 7:
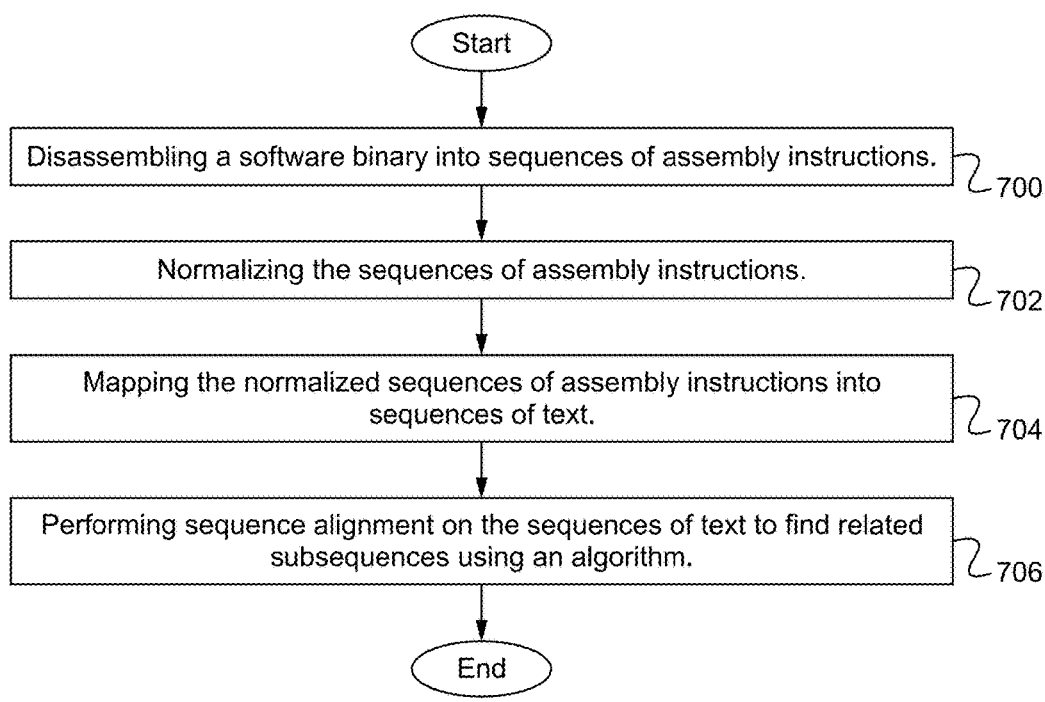
FIG. 7 illustrates a flowchart of a biosequence-based binary analysis method according to some embodiments.

FIG. 7 illustrates a flowchart of a biosequence-based binary analysis method according to some embodiments. In the step 700, a binary (e.g., a software binary, malware binary) is disassembled into sequences of assembly instructions. Disassembling is able to be automated to generate files properly formatted for sequence analysis.

In the step 702, the sequences of assembly instructions are normalized. Normalizing the sequences of assembly instructions includes removing all arguments and grouping similar opcodes categorically, mapping each category to a single letter. In some embodiments, finding related sequences includes grouping the opcodes into groups or bins. For example "move" opcodes are in one bin, and all "jump" opcodes are in another bin. The sequence of the opcodes is able to be referred to as the "protein."

In the step 704, the normalized sequences of assembly instructions are mapped into sequences of text.

In the step 706, sequence alignment is performed on the sequences of text to find related sequences using an algorithm (e.g., MadBlast). The algorithm is generalized to be applicable to string alphabets beyond a standard 20 amino acid characters. The string alphabets comprise approximately any printable ASCII character (e.g., any printable ASCII character (except for > and # which are used as part of the input files). In some embodiments, the sequences of text shorter than a first threshold are eliminated, and the sequences of text longer than a second threshold are separated into multiple sequences of a fixed length. The sequences of text longer than the second threshold are split based on the amount of memory available. In some embodiments, sequence alignment includes comparing the opcodes and generating a score based on the comparison, where the scores are used to group the proteins in families or clusters. Grouping similar opcodes categorically includes generating a representation for each cluster. Generating the representation for each cluster (e.g., motif) is by consensus or hidden mark off Consensus includes aligning items in the cluster and providing segments that align, and hidden mark off includes generating one or more profile of a cluster by finding segments that are the same and the segments that are different. In some embodiments, one protein represents a family of malware (e.g., one million pieces of malware are able to be turned into one thousand families, so one thousand representations are able to be used for one million pieces of malware which is a significant amount of data reduction). In some embodiments, the representations for each cluster are stored in a motif library which is able to be dynamic such that it grows based on new data/analysis. In some embodiments, the families and motifs are realigned based on new data/analysis. The data (e.g., representations) is able to be stored in a single file or multiple files on a storage device such as a portable storage device (e.g., a thumb drive).

In some embodiments, memory for Smith-Waterman calculations is allocated one time initially, and the memory is reused for each alignment. The size of the memory allocated is configurable. The algorithm utilizes a master/workers/tasks concept, where tasks are given by a master to worker cores. At startup, the master opens a query file and waits for requests, the worker cores allocate memory to run local Smith-Waterman calculations, and each worker core on a node allocates memory one at a time, and if there is not enough memory remaining, the worker cores that come online later do not allocate memory or run. As soon as a worker core allocates memory, the worker core requests a task from the master without waiting for other worker cores to allocate memory. Each node allocates a variable amount of worker cores and memory. If a worker core processes a query for longer than a threshold, the worker core asks the master for help, and if the other worker cores are still busy, the master refuses, otherwise, the master helps the worker core.

In some embodiments, fewer or additional steps are implemented. For example, in some embodiments, the sequences of text, a scoring matrix that contains reward values for text alignment and misalignment events and scoring parameters are received. In some embodiments, the scoring matrix is a plug and play scoring matrix based on an alphabet selected. In some embodiments, the method is implemented using parallel processing. In some embodiments, the order of the steps is modified.

In some embodiments, the representations are able to be used to detect malware. For example, when a binary is received (e.g., via email), the binary is disassembled and turned into a protein representation, compared against a library of representations (e.g., motif library), and if there is a match, then it is determined that the binary belongs to a specific malware family. Upon detecting a match, appropriate actions are able to be taken such as deleting the binary, quarantining the binary, sending an alert, and/or any other action. The biosequence-based binary analysis method is able to catch zero day malware.

In some embodiments, the biosequence-based binary analysis method is used to implement a whitelist—items that are allowed to be on a computer. The method analyzes binaries to ensure they are what they say they are. For example, does Version 3 of Program X look similar to Versions 1 and 2 or does it look like something not on the computer. If it looks similar, based on the analysis described herein, then the program is allowed to run, but if it does not look similar, then steps are able to be taken such as blocking the program from access, warning the user or a network administrator, and/or any other steps.

In some embodiments, server logs are analyzed by taking net flow (traffic data between networks), clustering some of the properties of net flow and generating proteins based on the net flow information. Examples of net flow properties include but are not limited to who is talking to whom, when was the connection made, how much data was sent/received, metadata of ports, IP and where from, and/or any other net flow data. The behavior of a user is able to be represented (such as user searches legal web pages, sends email), then it is determined if the entropy of what the user is doing changes, and if so, it is considered that the user's behavior has changed, and the change is noted (e.g., a flag is sent to a system administrator to perform further analysis).

To utilize the biosequence-based binary analysis method, binary data is analyzed (e.g., binary information is provided to an algorithm) which processes and classifies the information into bins and generates families of proteins which represent the binary data. The families of proteins are then able to be implemented to compare with incoming or new binary information to determine if the new binary information should be allowed to run or if the new binary information is malware, and if additional actions should be taken. In some embodiments, the monitoring/comparing processes are able to be implemented in the background of a computing device or at a network level so that an end user notices little, if any, difference in utilizing the computing device.

In operation, the biosequence-based binary analysis method enables analysis of information such as malware binaries or other software binaries. The biosequence-based binary analysis does not utilize an exact matching scheme, so better detection of slightly modified binaries is possible. Additionally, malware does not need to be run to perform the analysis, so the analysis is able to be implemented safely. Furthermore, by ignoring operands and by utilizing other improvements, the biosequence-based binary analysis is able to be executed efficiently and quickly.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A method programmed in a non-transitory memory of a device comprising:
   a. disassembling a software binary into sequences of assembly instructions;
   b. normalizing the sequences of assembly instructions;
   c. mapping the normalized sequences of assembly instructions into sequences of text; and
   d. performing sequence alignment on the sequences of text to find related subsequences using an algorithm, wherein the algorithm utilizes a master/workers/tasks concept, wherein tasks are given by a master to worker cores, wherein at startup, the master opens a query file and waits for requests, the worker cores allocate memory to run local Smith-Waterman calculations, wherein each worker core on a node allocates memory one at a time, and if there is not enough memory remaining, the worker cores that come online later do not allocate memory or run, further wherein as soon as a worker core allocates memory, the worker core requests a task from the master without waiting for other worker cores to allocate memory.

2. The method of claim 1 further comprising receiving the sequences of text, a scoring matrix that contains reward values for text alignment and misalignment events, and scoring parameters using the algorithm, wherein the scoring matrix is a plug and play scoring matrix based on an alphabet selected.

3. The method of claim 1 wherein the algorithm is generalized to be applicable to string alphabets beyond a standard 20 amino acid characters, wherein the string alphabets comprise approximately any printable ASCII character.

4. The method of claim 1 wherein disassembling is automated to generate files properly formatted for sequence analysis.

5. The method of claim 1 wherein normalizing the sequences of assembly instructions includes removing all arguments and grouping similar opcodes categorically, mapping each category to a single letter, wherein grouping similar opcodes categorically includes generating a representation for each cluster.

6. The method of claim 5 wherein generating the representation for each cluster is by consensus or hidden mark off, wherein consensus includes aligning items in the cluster and providing segments that align, and hidden mark off includes generating one or more profile of a cluster by finding segments that are the same and the segments that are different.

7. The method of claim 1 further comprising eliminating the sequences of text shorter than a first threshold, and separating the sequences of text longer than a second threshold into multiple sequences of a fixed length, wherein the sequences of text longer than the second threshold are split based on the amount of memory available.

8. The method of claim 1 further comprising allocating memory for Smith-Waterman calculations one time initially and reusing the memory for each alignment, wherein the size of the memory allocated is configurable.

9. The method of claim 1 wherein each node allocates a variable amount of worker cores and memory.

10. The method of claim 1 wherein if a worker core processes a query for longer than a threshold, the worker core asks the master for help, and if the other worker cores are still busy, the master refuses, otherwise, the master helps the worker core.

11. A system comprising:
a. a disassembler module configured for disassembling a software binary into sequences of assembly instructions;
b. a normalizing module configured for normalizing the sequences of assembly instructions;
c. a mapping module configured for mapping the normalized sequences of assembly instructions into sequences of text; and
d. an alignment module configured for performing sequence alignment on the sequences of text to find related subsequences using an algorithm, wherein the algorithm utilizes a master/workers/tasks concept, wherein tasks are given by a master to worker cores, wherein at startup, the master opens a query file and waits for requests, the worker cores allocate memory to run local Smith-Waterman calculations, wherein each worker core on a node allocates memory one at a time, and if there is not enough memory remaining, the worker cores that come online later do not allocate memory or run, further wherein as soon as a worker core allocates memory, the worker core requests a task from the master without waiting for other worker cores to allocate memory.

12. The system of claim 11 wherein the disassembler module is further configured for receiving the sequences of text, a scoring matrix that contains reward values for text alignment and misalignment events, and scoring parameters using the algorithm, wherein the scoring matrix is a plug and play scoring matrix based on an alphabet selected.

13. The system of claim 11 wherein the algorithm is generalized to be applicable to string alphabets beyond a standard 20 amino acid characters, wherein the string alphabets comprise approximately any printable ASCII character.

14. The system of claim 11 wherein disassembling is automated to generate files properly formatted for sequence analysis.

15. The system of claim 11 wherein normalizing the sequences of assembly instructions includes removing all arguments and grouping similar opcodes categorically, mapping each category to a single letter, wherein grouping similar opcodes categorically includes generating a representation for each cluster.

16. The system of claim 8 wherein generating the representation for each cluster is by consensus or hidden mark off, wherein consensus includes aligning items in the cluster and providing segments that align, and hidden mark off includes generating one or more profile of a cluster by finding segments that are the same and the segments that are different.

17. The system of claim 11 wherein the normalizing module is further configured for eliminating the sequences of text shorter than a first threshold, and separating the sequences of text longer than a second threshold into multiple sequences of a fixed length, wherein the sequences of text longer than the second threshold are split based on the amount of memory available.

18. The system of claim 11 wherein the alignment module is further configured for allocating memory for Smith-Waterman calculations one time initially and reusing the memory for each alignment, wherein the size of the memory allocated is configurable.

19. The system of claim 11 wherein each node allocates a variable amount of worker cores and memory.

20. The system of claim 11 wherein if a worker core processes a query for longer than a threshold, the worker core asks the master for help, and if the other worker cores are still busy, the master refuses, otherwise, the master helps the worker core.

21. An apparatus comprising:
a. a non-transitory memory for storing an application, the application for:
i. disassembling a software binary into sequences of assembly instructions;
ii. normalizing the sequences of assembly instructions;
iii. mapping the normalized sequences of assembly instructions into sequences of text; and
iv. performing sequence alignment on the sequences of text to find related subsequences using an algorithm, wherein the algorithm utilizes a master/workers/tasks concept, wherein tasks are given by a master to worker cores, wherein at startup, the master opens a query file and waits for requests, the worker cores allocate memory to run local Smith-Waterman calculations, wherein each worker core on a node allocates memory one at a time, and if there is not enough memory remaining, the worker cores that come online later do not allocate memory or run, further wherein as soon as a worker core allocates memory, the worker core requests a task from the master without waiting for other worker cores to allocate memory; and b. a processor coupled to the memory, the processor configured for processing the application.

22. The apparatus of claim 21 wherein the application is further configured for receiving the sequences of text, a scoring matrix that contains reward values for text alignment and misalignment events, and scoring parameters using the algorithm, wherein the scoring matrix is a plug and play scoring matrix based on an alphabet selected.

23. The apparatus of claim 21 wherein the algorithm is generalized to be applicable to string alphabets beyond a standard 20 amino acid characters, wherein the string alphabets comprise approximately any printable ASCII character.

24. The apparatus of claim 21 wherein disassembling is automated to generate files properly formatted for sequence analysis.

25. The apparatus of claim 21 wherein normalizing the sequences of assembly instructions includes removing all arguments and grouping similar opcodes categorically, mapping each category to a single letter, wherein grouping similar opcodes categorically includes generating a representation for each cluster.

26. The apparatus of claim 25 wherein generating the representation for each cluster is by consensus or hidden mark off, wherein consensus includes aligning items in the cluster and providing segments that align, and hidden mark off includes generating one or more profile of a cluster by finding segments that are the same and the segments that are different.

27. The apparatus of claim 21 wherein the application is further configured for eliminating the sequences of text shorter than a first threshold, and separating the sequences of text longer than a second threshold into multiple sequences of a fixed length, wherein the sequences of text longer than the second threshold are split based on the amount of memory available.

28. The apparatus of claim 21 wherein the application is further configured for allocating memory for Smith-Waterman calculations one time initially and reusing the memory for each alignment, wherein the size of the memory allocated is configurable.

29. The apparatus of claim 21 wherein each node allocates a variable amount of worker cores and memory.

30. The apparatus of claim 21 wherein if a worker core processes a query for longer than a threshold, the worker core asks the master for help, and if the other worker cores are still busy, the master refuses, otherwise, the master helps the worker core.

* * * * *